United States Patent [19]

Hibino et al.

[11] 4,153,610

[45] May 8, 1979

[54] PROCESS FOR PRODUCING 5-CARBOXY-2-ACETYLTHIOPHENE

[75] Inventors: Toshihiko Hibino, Takarazuka; Eiichi Murayama, Toyonaka, both of Japan

[73] Assignee: Sumitomo Chemical Company, Limited, Osaka, Japan

[21] Appl. No.: 847,617

[22] Filed: Nov. 1, 1977

[30] Foreign Application Priority Data

Nov. 22, 1976 [JP] Japan ................................ 51-140326

[51] Int. Cl.$^2$ ........................................... C07D 333/38
[52] U.S. Cl. ............................................. 260/332.2 C
[58] Field of Search ................ 260/332.3 R, 332.2 C, 260/523 R

[56] References Cited

PUBLICATIONS

Hartough, "Thiophene and Derivatives", (1952), p. 400.

*Primary Examiner*—A. Siegel
*Attorney, Agent, or Firm*—Wenderoth, Lind & Ponack

[57] ABSTRACT

5-Carboxy-2-acetylthiophene, which is useful as an intermediate for the production of a therapeutic agent, can be prepared in a high yield by the selective oxidation of 5-acetyl-2-thienylacetic acid or its derivative with a particularly selected oxidizing agent, i.e. permanganate.

7 Claims, No Drawings

PROCESS FOR PRODUCING 5-CARBOXY-2-ACETYLTHIOPHENE

The present invention relates to a process for producing 5-carboxy-2-acetylthiophene.

5-Carboxy-2-acetylthiophene has been known to be a useful intermediate for the production of the thienyl-thiazole derivative of the formula:

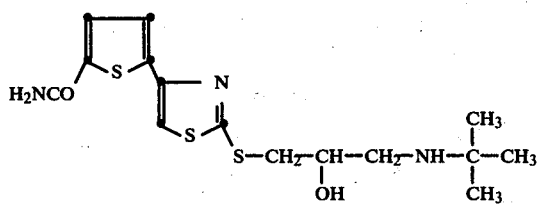

which is useful as a potent therapeutic agent for the treatment of heart diseases such as arrhythmia and coronary heart diseases (U.S. Pat. No. 3,932,400).

With respect to the preparation of 5-carboxy-2-acetylthiophene, there have been proposed the following processes:

(1) Hydrolysis of 5-cyano-2-acetylthiophene, [Linstead, Noble and Wright; J. Chem. Soc., 1937, 911. Dann; Ber., B76, 419 (1943)]

(2) Oxidation of 2,5-diacetylthiophene, [Hartough and Kosak; J. Am. Chem. Soc., 69, 1012 (1947)]

(3) Acylation of thenoic acid ester, [K. Schöegel and H. Pelonsek; Ann., 1 (1962)]

(4) Carboxylation of 2-methyl-2'-thienyl-1,3-dioxolane (acetylthiophen ketal). [Thames and McClesky; J. Heterocyclic Chem., 3, (1), 104 (1966)]

These known processes are, however, unsatisfactory for the commercial production of said compound.

So far, it has been quite difficult, or rather impossible to expect whether oxidation occurs at the acetyl methyl group or at the methylene group linked to the thiophene ring when 5-acetyl-2-thienylacetic acid or its derivative is subjected to the oxidation reaction.

As the result of a study, it has been found that 5-acetyl-2-thienylacetic acid or its derivative can selectively be oxidized with a permanganate to 5-carboxy-2-acetylthiophene, when the oxidation reaction is conducted under neutral or basic conditions. Specifically, 5-carboxy-2-acetylthiophene can advantageously be prepared in a high yield by the selective oxidation of 5-acetyl-2-thienylacetic acid of the formula (II):

(II)

with a permanganate under neutral conditions.

It can also be prepared in a high yield by the oxidation of 5-acetyl-2-thienylacetic acid derivative of the formula (III):

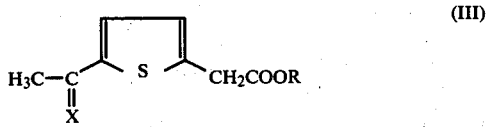

(III)

wherein X is a conventional carbonyl-protecting group, and R is a hydrogen atom or a conventional ester residue, with a permanganate under neutral conditions as well as basic conditions, and then removing the carbonyl-protecting group.

The term "conventional carbonyl-protecting group" as used herein means any carbonyl-protecting group which does not disturb the progress of the oxidation reaction and which is removable. Examples of such carbonyl-protecting group are ketal, hemithioketal, dithioketal, thiazolidine, imidazolidine and oxazolidine. The term "conventional ester residue" as used herein means any ester residue which does not disturb the progress of the oxidation reaction. Examples of such ester residue are lower alkyl (e.g. methyl, ethyl, etc.) and phenyl group.

The oxidation of 5-acetyl-2-thienylacetic acid with a permanganate can be conducted in ketone solvents in the presence of a carbonate (e.g. sodium carbonate, potassium carbonate, sodium bicarbonate, etc.), or in a buffer solution (e.g. phosphate buffer, Borax buffer, etc.) or a mixture of a buffer solution and a ketone solvent, while maintaining the reaction system neutral, preferably pH 6 to 8.

In case of the oxidation of the compound of the formula (III) as above, the reaction can be conducted under the same reaction conditions as described above, or it may be carried out in water, ketone solvents or a mixture thereof under basic conditions.

In the process of the present invention, the reaction temperature is not particularly limited, but it is preferable to carry out the reaction at a temperature from 0° to 100° C. in any case.

Examples of preferred permanganate are potassium permanganate and sodium permanganate.

In carrying out the process of the present invention, it is preferable to use 1.5 to 5 moles of a permanganate per 1 mole of 5-acetyl-2-thienylacetic acid or the compound of the formula (III).

After the reaction is finished, the carbonyl protecting group can be removed by a conventional method as disclosed in McOMIE; "Protective Groups in Organic Chemistry", Plenum Press London and New York (1973). For example, ketal, hemithioketal, oxazolidine and imidazolidine can be removed by treating them with a dilute acid (e.g. dil. hydrochloric acid, dil. sulfuric acid, aqueous acetic acid, etc.). [C. Djerassi, F. Batres, J. Romo and G. Rosenkranz; J. Am. Chem. Soc., 74, 3634 (1952). E. P. Goldberg and H. R. Nace; J. Am. Chem. Soc., 77, 359 (1955). H. W. Wanzlict and W. Loechell; Chem. Ber., 86, 1463 (1953)] Thioketal can be removed with a mercury salt. [H. Zinner, K. H. Rohde and A. Mattheus; Ann., 677, 160 (1964). E. J. Corey and R. B. Mitra; J. Am. Chem. Cos., 84, 2938 (1962)]

The isolation of the product can be carried out in a conventional manner. For example, well-refined 5-carboxy-2-acetylthiophene, which sometimes precipitates when the reaction system is acidified with a suitable acid such as hydrochloric acid, can be isolated by filtration and washing with water, or it may be isolated by extracting with an inert solvent such as ether or by evaporating the solvent and washing the product with water.

5-Acetyl-2-thienylacetic acid and the compound of the formula (III) can be prepared from 2-thienylacetic acid as follows:

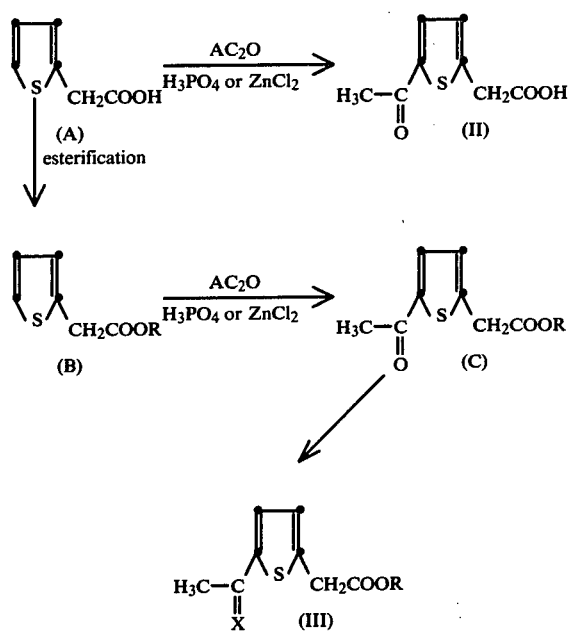

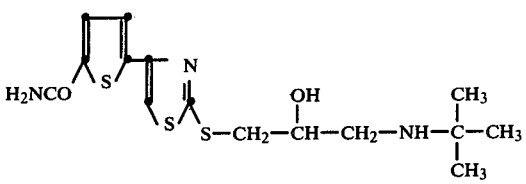

The compound (II) can be prepared by acylating 2-thienylacetic acid (A) with acetic anhydride in the presence of phosphoric acid or zinc chloride. The compound (C) can be obtained in the same manner as above from the compound (B), which can be prepared by the esterification of the compound (A). The compound (III) can be prepared by introducing the carbonyl-protecting group by a conventional method as disclosed in the "Protective Groups in Organic Chemistry".

As mentioned previously, 5-carboxy-2-acetylthiophene can be used as an intermediate for the production of a therapeutic agent, which can be prepared from 5-carboxy-2-acetylthiophene as follows:

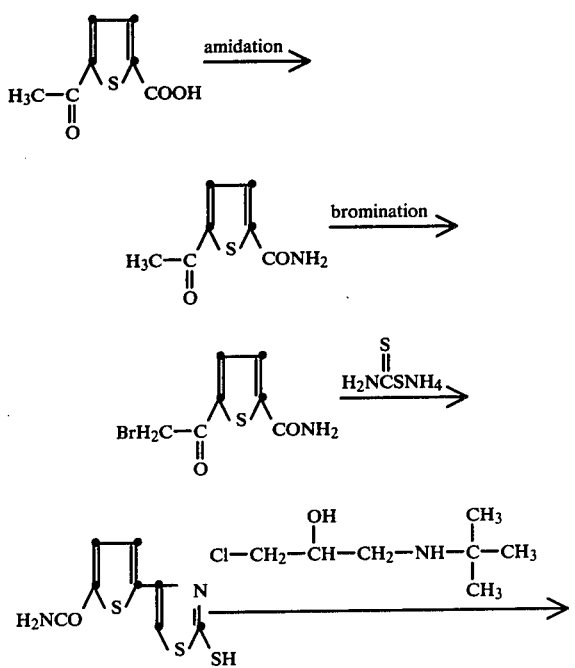

The following examples are given to illustrate the present invention more concretely, but it is not intended to limit the present invention thereto.

EXAMPLE 1

An emulsion of 5-acetyl-2-thienylacetic acid methyl ester ketal 57.0 g (0.236 mol) in an alkaline solution of 19.3 g (0.483 mol) of sodium hydroxide in 343 ml of water was heated at 60° C. for 0.5 hr., and successive addition of 74.4 g (0.471 mol) of potassium permanganate in 890 ml of hot water (~50° C.) was carried out between 60 and 70° C. After the addition was complete, the mixture was stirred at the same temperature for 3 hours. Manganese dioxide produced was removed by filtration. The filtrate was made acidic (pH 1) with 55.3 ml of conc. hydrochloric acid, condensed to a half volume and cooled. Precipitate was collected, washed with water and dried. Yield; 21.4 g (65%) This material was identical to an authentic sample (IR, NMR and mixed M.P.).

EXAMPLE 2

Ninety-two grams (0.5 mol) of 5-acetyl-2-thienylacetic acid was dissolved in 1.5 liters of acetone and 83 g. (0.6 mol) of potassium carbonate was added. To this cooled (0°-5° C.) suspension was added portionwise 100 g. (0.7 mol) of potassium permanganate with stirring under nitrogen. The mixture was stirred at room temperature for 2 hours. At this stage, 18.4 g. of potassium permanganate was added, stirring was continued for 3 more hours and finally the resulting mixture was heated under reflux for 1.5 hours. After complete cooling, 1.5 liters of water was added and manganese dioxide produced was removed by filtration. The filtrate was distilled until the temperature of distillate reached 100° C., cooled, made acidic with conc. hydrochloric acid and precipitate was collected. Yield; 55 g. (65%) This product was identical to an authentic sample (IR, NMR and mixed M.P.).

Preparation of 5-acetyl-2-thienylacetic acid methyl ester

A mixture of 2-thienylacetic acid methyl ester, 1.41 g. (0.01 mol) and acetic anhydride, 4.2 g. (0.04 mol) was heated at 70°-80° C. and 0.2 g. of 85% H$_3$PO$_4$ was added dropwise with mechanically stirring. The reaction was somewhat exothermic but cooling was not necessary. The mixture was maintained between 70°-80° C. for 3 hours, and then, poured onto ice-water followed by extraction with ether. Organic layer was washed with water several times, dried over anhyd. MgSO$_4$ and evaporated. The residue was distilled at 2mmHg and a fraction between 160° C. and 172° C. was collected. This material was gradually crystallized and could be recrystallized from the mixture of light-petroleum and benzene. m.p. 43°-44° C. Yield; 1.39 g. (76.5%)

Ketallization of 5-acetyl-2-thienylacetic acid methyl ester

A solution of ethyleneglycol, 0.997 g. (15.7 mmol) ethyl orthoformate, 1.307 g. (9.47 mmol), 5-acetyl-2-thienylacetic acid methyl ester, 0.572 g. (3.14 mmol) and a trace of p-toluenesulfonic acid was allowed to stand at room temperature for 3 hours. The mixture was poured into water and the organic layer was separated. The aqueous layer was extracted with benzene (50 ml × 2). Both organic layers were combined, washed with water, dried over anhyd. MgSO$_4$ and evaporated in vacuo to provide 0.286 g. (91%) of the ketal as a yellow oil. This product can be characterized as the ethylene ketal of 5-acetyl-2-thienylacetic acid methyl ester on the basis of disappearance of carbonyl absorbtion at 1670 cm$^{-1}$ (IR) and appearance of singlet of dioxolane methylene at 4.00 (δ) (NMR).

What is claimed is:

1. A process for producing 5-carboxy-2-acetylthiophene which comprises either (1) oxidizing a compound of the formula (III)

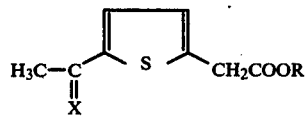

(III)

wherein X is oxygen or a conventional carbonyl-protecting group and R is hydrogen or a conventional ester residue, with a permanganate at a pH of 6 to 8 and a temperature of 0 to 100° C., and, if necessary, removing the carbonyl-protecting group, or (2) oxidizing a compound of the formula (III) wherein X is a conventional carbonyl-protecting group and R is hydrogen or a conventional ester residue, with a permanganate at a pH of higher than 8 and a temperature of 0° to 100° C., and removing the carbonyl-protecting group.

2. A process for producing 5-carboxy-2-acetylthiophene which comprises oxidizing 5-acetyl-2-thienylacetic acid with a permanganate at a pH of 6 to 8 and a temperature of 0° to 100° C.

3. The process according to claim 2, wherein the permanganate is potassium permanganate or sodium permanganate.

4. A process for producing 5-carboxy-2-acetylthiophene which comprises oxidizing a compound of the formula

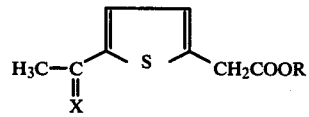

wherein X is a conventional carbonyl-protecting group and R is hydrogen or a conventional ester residue, with a permanganate at a pH of higher than 8 and a temperature of 0° to 100° C., and removing the carbonyl-protecting group.

5. The process according to claim 4, wherein the permanganate is potassium permanganate or sodium permanganate.

6. The process according to claim 4, wherein the reaction is conducted in water, a ketone solvent or a mixture thereof.

7. The process according to claim 2, wherein the reaction is conducted in a ketone solvent in the presence of a carbonate, or in a buffer solution or a mixture of a buffer solution and a ketone solvent.

* * * * *